(12) United States Patent
Jansen et al.

(10) Patent No.: US 11,406,091 B2
(45) Date of Patent: Aug. 9, 2022

(54) INSECT BREEDING DEVICE

(71) Applicant: Protix B.V., Dongen (NL)

(72) Inventors: Jaco Jansen, Breda (NL); Hendrikus Ant Schol, Waspik (NL); Bastiaan Frederik Jürgens, Rotterdam (NL)

(73) Assignee: Protix B.V., Dongen (NL)

( * ) Notice: Subject to any disclaimer, the term of this patent is extended or adjusted under 35 U.S.C. 154(b) by 137 days.

(21) Appl. No.: 16/955,059

(22) PCT Filed: Dec. 21, 2018

(86) PCT No.: PCT/NL2018/050870
§ 371 (c)(1),
(2) Date: Jun. 18, 2020

(87) PCT Pub. No.: WO2019/125165
PCT Pub. Date: Jun. 27, 2019

(65) Prior Publication Data
US 2021/0007335 A1   Jan. 14, 2021

(30) Foreign Application Priority Data

Dec. 22, 2017 (NL) .................................... 2020154

(51) Int. Cl.
*A01K 67/033*   (2006.01)
*A01K 1/01*   (2006.01)

(52) U.S. Cl.
CPC .............. *A01K 67/033* (2013.01); *A01K 1/01* (2013.01)

(58) Field of Classification Search
CPC ................................ A01K 67/033; A01K 1/01

USPC ............................................ 119/6.5, 6.6, 246
See application file for complete search history.

(56) References Cited

U.S. PATENT DOCUMENTS

| | | | | |
|---|---|---|---|---|
| 5,178,094 A * | 1/1993 | Carr | ...................... | A01K 67/033 119/6.5 |
| 5,771,841 A * | 6/1998 | Boor | ...................... | A01K 1/0107 119/452 |
| 6,041,741 A * | 3/2000 | Gabriel | .................. | A01K 1/031 119/417 |
| 6,588,373 B1 * | 7/2003 | Strzempko | ........... | A01K 1/0245 119/416 |
| 2003/0150394 A1 * | 8/2003 | Wolfe | .................. | A01K 63/003 119/246 |

(Continued)

FOREIGN PATENT DOCUMENTS

| | | |
|---|---|---|
| CN | 206284043 U | 6/2017 |
| FR | 3046333 A1 | 7/2017 |

(Continued)

*Primary Examiner* — Yvonne R Abbott-Lewis
(74) *Attorney, Agent, or Firm* — N.V. Nederlandsch Octrooibureau (57) ABSTRACT

The invention relates to an insect breeding device. The insect breeding device comprising at least one insect cage; a bin for holding a cleaning liquid; a first pipe connected to the bin for receiving the cleaning liquid, wherein the pipe is entering the at least one insect cage through a first opening; a nozzle, coupled to the first pipe, positioned inside the at least one insect cage configured to deliver the cleaning liquid to the interior of the at least one insect cage; and a second pipe, coupled to a second opening, different from the first opening, in the at least one insect cage, configured to drain the cleaning liquid and the debris from the at least one insect cage.

21 Claims, 5 Drawing Sheets

(56) References Cited

U.S. PATENT DOCUMENTS

2017/0311612 A1* 11/2017 Leo .................. A21D 2/34

FOREIGN PATENT DOCUMENTS

WO        02087321  A2    11/2002
WO     2016166465  A1    10/2016

* cited by examiner

INSECT BREEDING DEVICE

TECHNOLOGICAL FIELD

The invention relates to an insect breeding device used for insect breeding.

BACKGROUND

Rearing and breeding insects at an industrial and economically feasible scale is gaining momentum for its potential as an alternative source of animal lipids, fat, proteins, amino-acids, fatty acids, etc., compared to those currently provided by, for example, the livestock industry. However, bringing the current state of the art of insect farming, especially the breeding of insects, from a small scale to such an industrial scale poses challenges not encountered in research currently done in the laboratory. Known methods for farming insects are, for example, labor-intensive with at best a handful of aspects being automated.

One of the major drawbacks of scaling up a known insect breeding device is that there are no suitable methods or means for efficaciously cleaning insect cages.

SUMMARY

It is an object of the invention to provide a solution to at least some of the aforementioned drawbacks of small-scale insect farming, especially the breeding of insects, in view of scaling up to a scale that is economically feasible.

In a first aspect of the invention this object is achieved by an insect breeding device comprising at least one insect cage, a bin for holding a cleaning liquid, a first pipe connected to the bin for receiving the cleaning liquid, wherein the pipe is entering the at least one insect cage through a first opening in the at least one insect cage, a nozzle, coupled to the first pipe, positioned inside the at least one insect cage configured to deliver the cleaning liquid to the interior of the at least one insect cage, and a second pipe, coupled to a second opening in the at least one insect cage, different from the first opening, in the at least one insect cage, configured to drain the cleaning liquid and debris remaining from farming insects in the insect cage from the at least one insect cage. This arrangement enables efficient cleaning of the one or more insect cages, the cleaning liquid is entered that is sprayed to the interior via the nozzle, the cleaning liquid removes the debris from the interior and is drained via the second opening.

Having clean cages for breeding insects is a prerequisite for successful egg harvesting, and therefore there is a need to clean the insect cage at the start of the insect breeding cycle when re-using the cages from a previous insect breeding cycle. Without discarding, for example, the remains of the pupae after adult insects emerged from these, i.e. the pupal exoskeleton or exuvia, and without discarding the dead insects, feces, uncollected eggs and insects that are still alive, from the cage before loading the cage with fresh pupae reduces the chance of an efficient egg harvest, and may even hamper the ability to harvest any insect eggs at all. That is to say, gravid female insects, such as black soldier flies, are tempted to lay eggs (referred to as "ovipositioning") in the vicinity of or in any suitable food source for the eggs to hatch. The olfactory attractant emerging from exuvia and dead insects stimulate the gravid flies to oviposition in areas of the cage other than at the desired location for ovipositioning, i.e. the "ovisite". Thus, the most likely consequence of not thoroughly cleaning the cage is sub-optimal egg collection. Currently, thorough cleaning of insect cages is a time and labor intensive activity, and hampers the scaling-up of insect breeding and egg collection at an industrial scale. Of course, insufficient cleaning of the cages also introduces the risk of emerging diseases, growth of microbes such as bacteria, yeasts and mold, for adversely influencing the insect colony.

In a preferred embodiment, the insect breeding device further comprises a gas drying apparatus comprising a ventilator for generating a gas flow, a heater for heating the generated gas flow, a third pipe coupled to a third opening of the insect cage for transporting the heated gas flow inside the at least one insect cage, and a fourth opening of the insect cage for transporting the gas out of the at least one insect cage. The heated gas, for example air, enables fast drying of the interior of the insect cage.

In a still further embodiment, the insect breeding device further comprises a liquid clearance device coupled to the second pipe and the bin, provided with a filter configured to separate the cleaning liquid from the debris and to deliver the cleaning liquid to the bin through a fifth pipe. This arrangement enables recycling of the cleaning liquid.

In one embodiment the filter comprises a sieve configured to separate the debris from the cleaning liquid, and a debris receptacle configured to collect the debris separated by the sieve.

In further embodiment, the cleaning liquid comprises water and at least one non-foaming detergent.

In further embodiment the cleaning liquid comprises between 0.5 percent and 10 percent of the non-foaming detergent by volume of the total cleaning liquid.

In a further embodiment the cleaning liquid comprises of a mixture of potassium, amine compounds, silicates, phosphates, non-ionogenic and amphoteric humidifiers and complexing agents.

In a further embodiment the nozzle is a fluid nozzle comprising one of a spiral liquid spray nozzle, a full-cone nozzle, a deflector plate nozzle, a solid jet nozzle, and a nozzle with a rotating head. One of the nozzles can be selected and mounted in the insect cage for efficient cleaning.

In a further embodiment, the insect breeding device further comprises a first pump, positioned between the first opening and the bin, configured to deliver cleaning liquid to the interior of the at least one insect cage with at least one of a predetermined flow rate and a predetermined liquid pressure.

In an embodiment the pressure of the cleaning liquid transported by the first pump is in the range between 1.5 and 6 bar.

In an embodiment the volume of cleaning liquid delivered into the at least one insect cage is in the range between 10 and 500 liters per minute.

In a further embodiment, the insect breeding device further comprises a second pump, positioned between the second opening and the bin, configured to transport the cleaning liquid and debris from the at least one insect cage to the bin.

In a further embodiment, the insect breeding device further comprises a third valve coupled to the third opening configured to open or close the third opening, and a fourth valve coupled to the fourth opening configured to open or close the fourth opening.

In a further embodiment, the insect breeding device further comprises a controller connected to the first valve and the second valve and the first pump and second pump, wherein the controller is arranged to switch between a first state and a second state, wherein in the first state the first and second valves are closed and the first and second pumps are switched off, and in the second state, wherein the first valve is open and the second valve is open, the first pump is switched on and the second pump is switched on, and the controller is further arranged to control the first pump to transport the cleaning liquid at a predetermined flow rate and pressure through the nozzle, and to control the second pump to transport the cleaning liquid and debris from the second opening to the liquid clearing device.

In a further embodiment the controller is further arranged to maintain the second state for a period between 20 and 120 minutes.

In one embodiment, the insect breeding device further comprises a heater, wherein the heater is arranged to deliver the cleaning liquid to the first pump at a temperature in the range of 31.5° C. and 32° C. A further advantage is that the heater comprised by the insect breeding device is also applicable for providing cleaning liquid to the first pump at a different temperature, such as between 15° C. and 31.5° C., such as about 25° C., and such as 32° C.-65° C., for example about 35° C. or 50° C.

In a further embodiment, the insect breeding device, wherein the at least one insect cage is arranged to have round corners in the inner surface of the cage.

In a further embodiment, the at least one insect cage is manufactured using rotation molding, of a polymer blend, preferably comprising polyethylene.

In a further embodiment, the at least one insect cage is further configured to have inner dimensions of a width between 30 cm and 150 cm, a depth between 50 cm and 200 cm and a height between 10 cm and 60 cm, In a further embodiment, the at least one insect cage further comprises a tapered surface on the surface coupled to the second opening.

In a further embodiment, the second opening is configured to have a width between 2 cm and 14 cm, preferably between 3 cm and 10 cm, more preferably around 5 cm.

In a further embodiment, the nozzle is further configured to have a spray angle between 240° and 300°, preferably about 270° for a solid nozzle, or between 90° and 120° for a spiral nozzle, and a spray pattern arranged as a solid cone or solid jets from a sphere.

In further embodiment, the nozzle is arranged to be positioned centrally in the inner volume of the at least one insect cage.

In a different embodiment, the insect breeding device comprises a further nozzle, both nozzles positioned off-center, in the inner volume of the insect cage.

In a further embodiment, the insect breeding device comprises at least two insect cages that are stacked with each other. In this arrangement multiple insect cages can be arranged in a horizontal or vertical direction so that a space efficient arrangement can be obtained.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not necessarily correspond to actual reductions to practice of the invention.

Furthermore, the terms first, second, third and the like in the description and in the claims, are used for distinguishing between similar elements and not necessarily for describing a sequential or chronological order. The terms are interchangeable under appropriate circumstances and the embodiments of the invention can operate in other sequences than described or illustrated herein.

Moreover, the terms top, bottom, over, under and the like in the description and the claims are used for descriptive purposes and not necessarily for describing relative positions. The terms so used are interchangeable under appropriate circumstances and the embodiments of the invention described herein can operate in other orientations than described or illustrated herein.

Furthermore, the various embodiments, although referred to as "preferred" or "e.g." or "for example" or "in particular" are to be construed as exemplary manners in which the invention may be implemented rather than as limiting the scope of the invention.

The term "comprising", used in the claims, should not be interpreted as being restricted to the elements or steps listed thereafter; it does not exclude other elements or steps. It needs to be interpreted as specifying the presence of the stated features, integers, steps or components as referred to, but does not preclude the presence or addition of one or more other features, integers, steps or components, or groups thereof. Thus, the scope of the expression "a device comprising A and B" should not be limited to devices consisting only of components A and B, rather with respect to the present invention, the only enumerated components of the device are A and B, and further the claim should be interpreted as including equivalents of those components.

The present invention is an insect breeding device that allows the cleaning of insect cages at a large scale. Use of the insect breeding device makes cleaning of the insect cage by hand superfluous, i.e. demands less labor. Furthermore, with the insect breeding device of the invention, cleaning multiple insect cages becomes controllable with regards to, for example, the intensity of the cleaning cycle and the timing of the procedure on a cage-by-cage basis. An important advantage of the insect breeding device of the invention is its applicability and suitability for use in cleaning insect cages impermeable for fluid and applicable for industrial scale breeding of insects.

Figure 1:
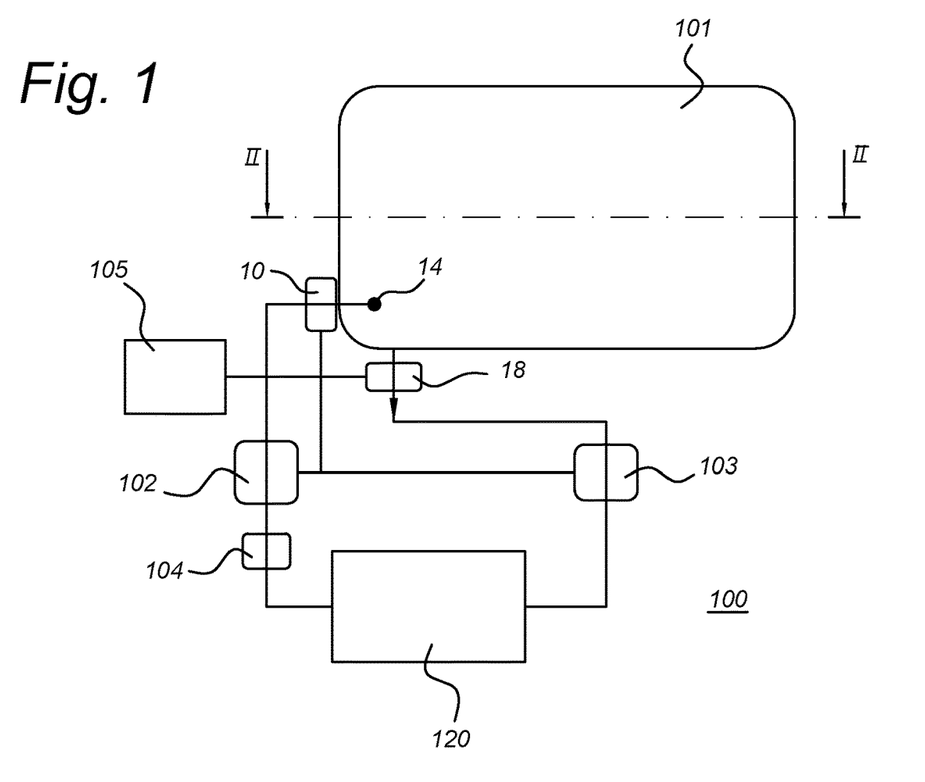
FIG. 1 illustrates a first embodiment of an insect breeding device of the present invention.
Figure 2:
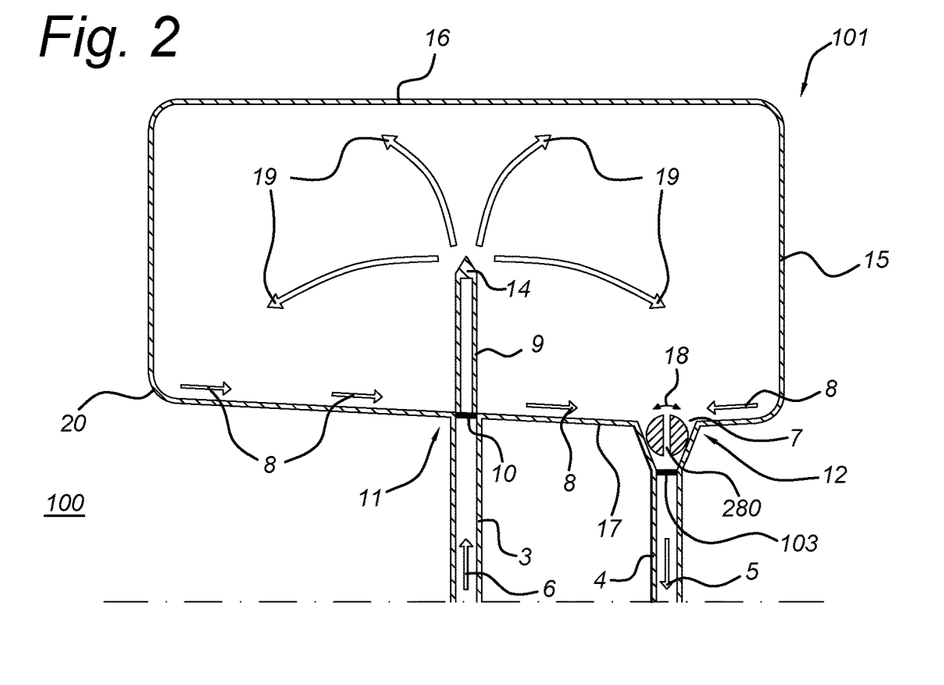
FIG. 2 illustrates an embodiment of an insect cage of the present invention.

FIG. 1 and FIG. 2 show the insect breeding device 100 according to a first embodiment of the present invention. The insect breeding device comprises an insect cage 101 with a bin 120 for holding cleaning liquid. A pipe 3 is connected from the bin 120 to the first opening 11 of the insect cage 101. A nozzle 14, coupled to the first pipe 3, is positioned inside the insect cage and is configured to deliver cleaning liquid to the interior of the insect cage. A second pipe 4 connects the second opening 12 of the insect cage 101 to the bin 120.

The cleaning liquid flows from the bin through the first pipe into the nozzle (arrow 6), positioned inside the at least one insect cage, in order to clean the inner surface of the insect cage. During the cleaning process, the cleaning liquid collects debris, such as dead insects and uncollected eggs as described above, that was present in the insect cage. This mixture of cleaning liquid and debris can then be expelled from the inside of the insect cage through the second pipe to for example the bin 120 (direction of arrow 5). In one embodiment, a pump 102, positioned between the bin 120 and the insect cage 101, is configured to deliver cleaning liquid to the interior of the insect cage with at least one of a predetermined flow rate and a predetermined liquid pressure.

An example of such an insect breeding device is the insect breeding device comprising at least one insect cage; a bin for holding a cleaning liquid; a first pipe connected to the bin for receiving the cleaning liquid, wherein the pipe is entering the at least one insect cage through a first opening in the at least one insect cage; a nozzle, coupled to the first pipe, positioned inside the at least one insect cage configured to deliver the cleaning liquid to the interior of the at least one insect cage; and a second pipe, coupled to a second opening in the at least one insect cage, different from the first opening in the at least one insect cage, configured to drain the cleaning liquid and debris remaining from farming insects in the insect cage from the at least one insect cage.

FIG. 2 shows insect cage 101 in the insect breeding device according to an embodiment of the invention. The insect cage 101 has a closed top wall 16. FIG. 2 shows schematically flows 19 of cleaning liquid so that any remains of the insect colony after death of said colony is removed from the inner surfaces 15 of the round cornered cages 101. Such remains include feces, dead insects, eggs ovipositioned outside the ovisite, pupae exoskeletons, dead pupae, etc. (debris).

In this embodiment the cleaning liquid can be flushed through the insect cage 101 after insects die inside the cage. In one embodiment, the cleaning liquid is water. In another embodiment, the cleaning liquid comprises a mixture of water and at least one detergent. Preferred detergents for application in the cleaning liquid used for cleaning using the insect breeding device are non-foaming detergents, although foaming detergents are also applicable in the cleaning liquid. In an embodiment the cleaning liquid comprises between 0.5% and 10% non-foaming detergent by volume of the cleaning liquid. In one embodiment, the cleaning liquid is an aqueous solution comprising less than 1.5% non-foaming detergent by volume of the total cleaning liquid. In a further embodiment, the cleaning liquid is an aqueous solution comprising about 1.0% non-foaming detergent by volume of the total cleaning liquid.

The fluid nozzle 14 can be a spiral water spray nozzle, a full-cone nozzle, one or two full cone nozzles, a deflector plate nozzle, a solid jet nozzle. The nozzle 14 is for example positioned at the distal end of a pipe 9 connecting the nozzle and pipe 3, relative to the first opening 11 in the bottom wall of the cage 101. The position inside the insect cage is such that in operation the complete surface of the inner side of the insect cage is contacted with the cleaning liquid 19, i.e., expelled at for example a pressure of about 3 bar, for example for about 50 minutes, at a speed of between about 10 liter/minute and 500 liter/minute, preferably between 30 liter/minute and 180 liter/minute, more preferable between 60 liter/minute and 80 liter/minute, such that for example the insect cage is cleaned with a volume of cleaning liquid such as a mixture of water and detergent, of between 500 liter and 25.000 liter, such as for example a preferred volume of about 3.500 liter when the insect cage has an inner volume of about between 100.000 cm$^3$ and 1.000.000 cm$^3$, preferably about 900.000 cm$^3$. In an embodiment, the nozzle is a rotating head, capable of rotating at low rate and expelling less fluid per minute than the spiral nozzle.

Technical details and performance details related to a preferred nozzle for application in the insect breeding device, such as a spiral nozzle or a solid jet nozzle, which is preferred, are:

Flow rate range: between 60 L/min and 100 L/min at 2.5 bar, preferably about 80 L/min;

Spray angle: between 240° and 300°, preferably about 270° for a solid nozzle, or between 120° and 90° for a spiral nozzle; and Spray pattern: Full cone or solid jets from a sphere.

In one embodiment, the insect breeding device of the present invention comprises a single nozzle 14 positioned centrally in the inner volume of the insect cage. The nozzle is coupled to a rigid pipe or tube 3 for example made of metal or a polymer, said pipe or tube entering the cage inner volume either through the top wall of the insect cage, from above, or through opening 11 in the floor 17 of the insect cage, from below. Alternatively, the pipe or tube enters the insect cage through an opening in a side wall of the cage. Positioning the nozzle in the middle of the insect cage volume contributes to the efficiency of the cleaning. In one embodiment, the insect cage comprises at least two nozzles, preferably two nozzles positioned off center in the inner volume of the insect cage, for example at positions in the floor located between 25% and 75% of the depth of the insect cage. In this arrangement the two nozzles in operation during a cleaning cycle generates a cyclone of washing solution or water near and in the drain.

The insect cage can be provided with at least one, preferably a single floor drain located in the second opening 12. The diameter of the circular drain opening in the floor can be between 2 cm and 14 cm, preferable between 3 cm and 10 cm, more preferably about 5 cm. Preferably, the insect cage has a block shape with rounded corners 20. Sharp edges between the opening of the drain and the floor of the cage are obeyed, as well as the presence of any recess or ridge in the side of the opening. It appears that gravid female insects, e.g. gravid female black soldier flies, are in this embodiment prevented from deposition of their eggs in the opening or close proximity of the opening, since the provision of a perceived shelter, for example under a ridge, in a recess, in the opening below floor level, etc., for the eggs is prevented.

The floor drain is configured such that cleaning the insect cage, does not cause the drain 280 to clog. In an embodiment the drain of the insect cage comprises a ball valve 7, since a ball valve has less tendency to clog by particulates present in the drained fluid. Alternatively, a butterfly valve can be applied.

The drain 280 inside the insect cage is positioned centrally in the floor part of the insect cage. Alternatively, the drain inside the insect cage can be located off center in the floor of the insect cage, such as in a corner. In an embodiment the insect breeding device can be provided with multiple drains in the floor of the insect cage. In a further embodiment, the floor part of the insect cage is tapered, having an amount of slope descending from the location of the side walls of the cage in the direction of the floor drain(s). Herewith, drainage 8 of the cleaning liquid is ensured during a washing cycle. In one embodiment, the insect cage can be provided with least one drainage opening 12, positioned off center in the floor surface. For example, the opening or openings such as two openings for draining fluid during cleaning of the cage is/are located in a portion of the floor of the cage located between 5 cm and 20 cm from the side walls of the cage. When two or more openings for draining the cleaning liquid are provided in the floor of the insect cage, the openings can be evenly spaced in said floor surface. In one embodiment, the insect breeding device further comprises of a second pump 103, positioned between the second opening of the insect cage and the bin 120, the second pump is configured to transport the cleaning liquid and debris from the at least one insect cage 101 to the bin 120.

In one embodiment, the insect breeding device typically flushes the inside of the insect cage with the cleaning liquid exiting from the first opening in the insect cage at a pressure of between 1.5 bar and 6 bar, preferably between 2 bar and 3 bar.

The insect breeding device typically flushes the batches of insect cages for a period between 20 minutes and 120 minutes, preferably between 30 minutes and 90 minutes, more preferably for between 40 minutes and 60 minutes, wherein each batch comprises between 2 and 20 cages, preferably 4 cages. On average, preferably the insect breeding device typically flushes between 5 and 20 cages per hour, such as about 8 to 14 cages per hour, preferably about 11 cages per hour.

In an embodiment of the present invention, the insect cage comprises a first valve 10, coupled to a first opening 11 of the insect cage, configured to open or close the first opening, and a second valve 18, coupled to a second opening of the insect cage, configured to open or close the second opening.

In one embodiment, the insect breeding device comprises a controller 105 connected to the first valve and the second valve and the first pump and the second pump, wherein the controller can switch between a first state and a second state. In the first state the first and second valves 10, 18 are closed and the first and second pumps 102, 103 are switched off. This first state represents when the insect cage does not require cleaning, and it is not possible to deliver or expel cleaning liquid into and from the insect cage. In the second state, the first valve is open and the second valve is open, the first pump is switched on and the second pump is switched on. In the second state the cleaning liquid is delivered into the insect cage and the cleaning liquid, and debris, is flushed out of the insect cage.

In one embodiment, the insect breeding device comprises a heater 104 arranged between the bin 120 and first pump 102. The heater is arranged to heat the cleaning liquid delivered to the first pump at a temperature in the range of 31.5° C. to 32° C.

Figure 3:
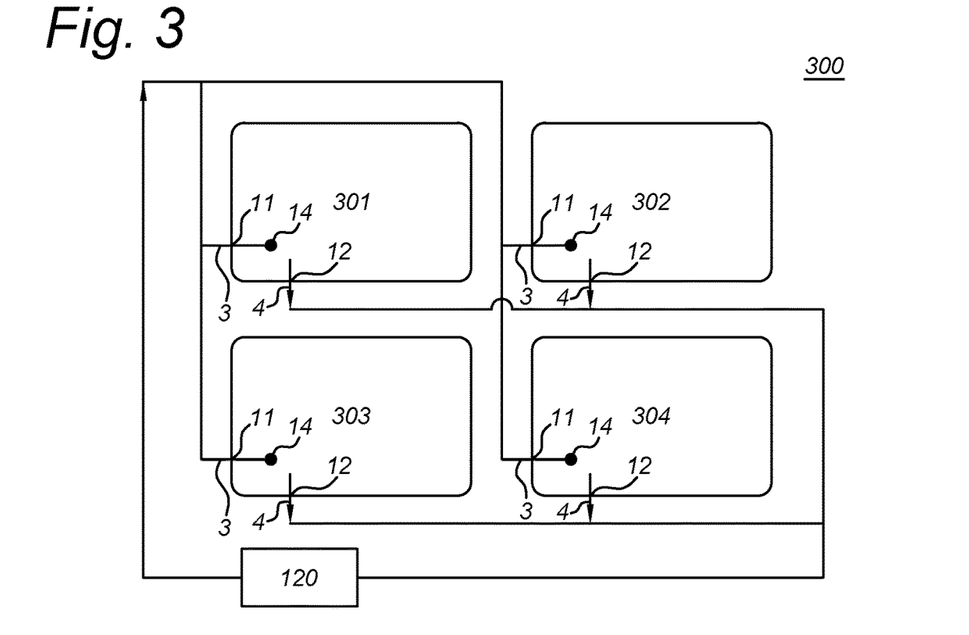
FIG. 3 illustrates an embodiment of an insect breeding device comprising of more than one cage.

FIG. 3 shows an insect breeding device 300 provided with four insect cages 301, 302, 303, 304 according to a second embodiment of the invention. All four insect cages are connected to the same bin 120. However, the total number of cages of the insect breeding device is not restricted to four. The insect cages in this embodiment are similar to those as described hereinbefore, for example insect cage 101.

Furthermore, the controller is arranged to control the first and second valves of the insect cages and the first and second pump.

The controller can be further arranged to clean one or more cages simultaneously, or in batches, or individually, with reduced reliance on labor and at increased speed during the cleaning step.

In one embodiment, wherein the insect breeding device has a multiple cages, the insect breeding device can have a cleaning capacity of between 2 cages/hour and 50 cages/hour, preferably between 5 cages/hour and 25 cages/hour, more preferably between 8 cages/hour and 16 cages/hour. In one embodiment, the insect breeding device can have a cleaning capacity for batch wisely washing at least 2 cages simultaneously, preferably at least 4 cages simultaneously, more preferably at least 10 cages simultaneously, most preferably at least 20 cages simultaneously.

For example, the insect breeding device may comprise, about one hundred horizontally and vertically stacked insect cages in an insect farming room such as a climate room for breeding insects, and can be cleaned without the need to displace the insect cages for the purpose of cleaning.

Typically, stacked insect cages provided with the insect breeding device have round-corners on the inner surface of insect cages (hereafter referred to as "round cornered cages"). Such round cornered cages contribute to preventing gravid female insects from ovipositioning at the corners of the insect cages. An advantage of such round cornered inner cage walls is its contribution to the efficiency of the cleaning operation of the insect breeding device.

The round cornered cages that are provided with the insect breeding device are preferably produced by rotation molding. Rotation molding provides cages with an inner surface of the side walls, top and floor that is particularly smooth. Such smooth surfaces contribute to the cleaning efficiency of the insect breeding device.

In one embodiment, the round cornered cages provided with the breeding device of the invention are made of a polymer or a polymer blend, preferably the cages are made of a polymer blend comprising polyethylene. In one embodiment, the round cornered cages provided with the breeding device of the invention are made of polyethylene. In one embodiment, said round cornered cages are made by rotation molding a blend of polyethylene, according to the invention. In one embodiment, said round cornered cages are made by rotation molding medium density polyethylene, according to the invention. In one embodiment, the round cornered cages provided with the breeding device of the invention are made of polypropylene.

Typically, a plurality of insect cages provided with the insect breeding device of the present invention have an inner size suitable for farming between 500 and 50.000 adult insects, such as between 1.000 and 20.000 adult insects. Typically, the round cornered cages for farming adult insects such as black soldier flies and for collecting the eggs derived therefrom, have inner dimensions of between 30 cm and 150 cm (width), between 50 cm and 200 cm (depth), and between 10 cm and 100 cm (height). Preferably, such round cornered cages provided with the insect breeding device of the present invention are substantially block shaped, typically with the following dimensions: about 120 cm (width), about 50 cm (height), 170 cm (depth). Preferred is a cage with a width of about 110 cm, a height of about 70 cm and a depth of about 160 cm.

Conventional cleaning of the insect cages one by one would require about between 6 minutes up to 12 minutes, and typically about 10 minutes on average of labor. Applying the automated and controllable insect breeding device of the present invention reduces the required time for cleaning a single insect cage to between 40 minutes and 60 minutes, on average, for cleaning for example between 4 and 20 cages simultaneously. Furthermore, the insect breeding device can wash multiple cages simultaneously, thus there is a significant gain in time required for cleaning cages when compared to individually cleaning cages by hand.

Conventional cleaning of insect cages by hand requires about between 150 liters and 250 liters of cleaning liquid, i.e. water comprising at least one detergent, preferably non-foaming detergent, or water per cage, and about 200 liters on average per insect cage. Preferably, the non-foaming detergent is for example Ecofoam, preferably about 1.0% Ecofoam by volume of the total cleaning liquid. Applying the insect breeding device of the present invention reduces the amount of cleaning liquid or water required to clean a single cage to between about 60 liters and 150 liters, such as for example a preferred volume of between about 70 liters and 140 liters per insect cage, more preferably between 80 liters per insect cage and 130 liters per insect cage according to the invention, such as about 90 liters per insect cage or about 110 liters per insect cage. Typically, according to the invention, the nozzle such as a spiral nozzle head, delivers about 60 liters per minute to 90 liters per minute water or cleaning liquid for a period of about one hour, preferably about 80 liters per minute according to the invention.

Figure 4:
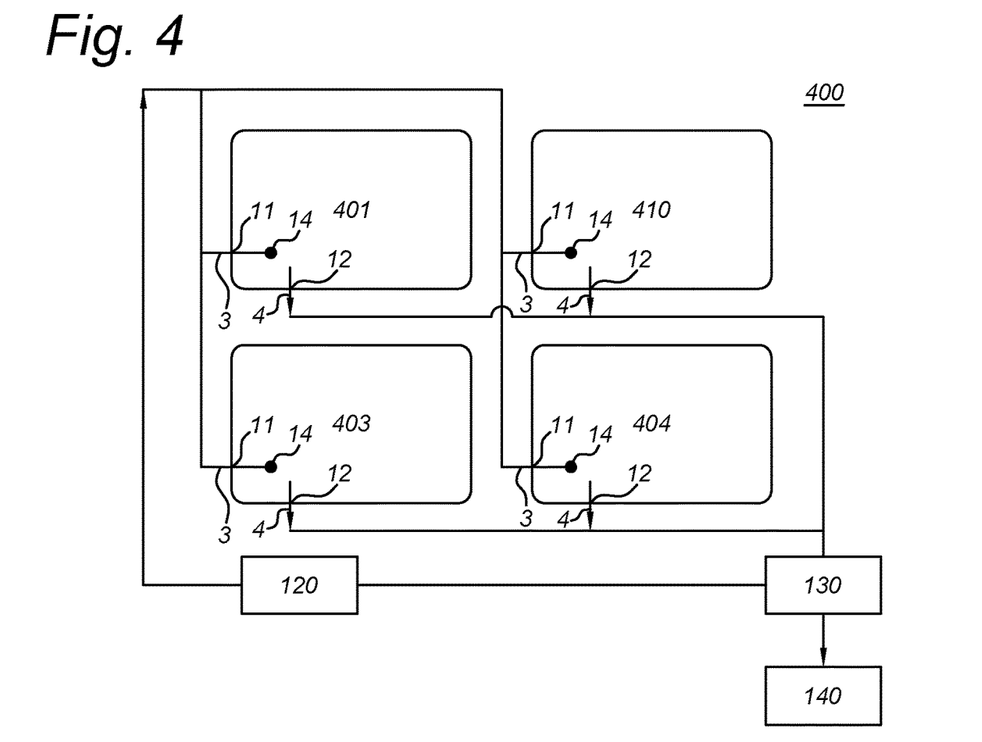
FIG. 4 illustrates an embodiment of an insect breeding device.

FIG. 4, shows an insect breeding device 400 with four insect cages 401, 410, 403, 404 according to a third embodiment of the invention. The insect cages in this embodiment are similar to those as described hereinbefore, for example insect cages 101, 301-304. Furthermore, in this embodiment at least part of the cleaning liquid used for cleaning the insect cage with the insect breeding device is re-used.

Preferably, between 10% and 100% of the cleaning liquid or water is re-used, for example between 25% and 80%. In one embodiment, for example 100% of the cleaning liquid is re-used for cleaning between 28 and 136 cages, such as about 64 cages, said cages cleaned in batches of 4 cages simultaneously, and for example subsequently 100% of water is re-used for rinsing the between 28 and 136 cages, such as about 64 cages, said cages again cleaned in batches of 4 cages simultaneously. For the purpose of recycling water or cleaning liquid, the insect breeding device 400 further comprises a liquid clearance device 130. The liquid clearance device 130 comprises a solid particle separation member such as a filter, a mesh, a screen, preferably a mesh, and/or such as a centrifugation arrangement. In one embodiment, the filter of the insect breeding device of the present invention comprises an angled sieve for separating liquids after cleaning from particulates. Such an angled sieve is a sieve that is tilted at an angle alpha relative to the horizontal, such that fluid such as the water or the cleaning liquid collected after cleaning the insect cage passes through the sieve and particles remain on top of the sieve, and said particles slide down the angular slope of the sieve towards for example a debris receptacle 140.

After clearing the used water or cleaning liquid that was collected after cleaning an insect cage, from solid particles originating for example from feces, uncollected eggs, dead insects, pupae remains, etc., said cleared fluid is at least in part reintroduced in the cage washing system, for re-use in a subsequent cleaning cycle. Optionally, the water or cleaning liquid cleared from particulates is first further cleaned from e.g. dissolved or dispersed contaminations, before being re-introduced in a cleaning cycle. Such a cleaning step is for example a ramp sieve whereby exuvi, etc. are sieved on a ramp and slide to a collection area while the cleaning liquid falls through the sieve and is re-used. Such a cleaning step comprising separating solution from solid particles is essential when water or cleaning liquid is applied during a cleaning cycle with a first batch of cages using the insect cage washer of the invention, and is re-used in a cleaning cycle with a further batch of cages. Optionally, cleaning liquid or water cleared after use in a cleaning cycle, is first stored before being applied in a next cleaning step. Thus, optionally, the insect breeding device of the present invention further comprises a liquid tank.

One of the many advantages of the insect breeding device of the present invention is the safety that is provided to workers involved in the farming of insects including cleaning of insect cages between two subsequent cycles of breeding, with regard to the reduced risk of contact with irritants. Since the insect breeding device is a closed system, exposure of detergents present in the cleaning liquid to the environment is limited, contributing to a safe working environment in the insect farming room.

Before an insect cage is used in a first or subsequent round of an insect breeding cycle starting from the pupae stage up to death of the adult insect after mating and the gravid female insects having ovipositioned, the applied insect cage preferably has a dry inner surface cleared from droplets of fluid such as water.

Figure 5:
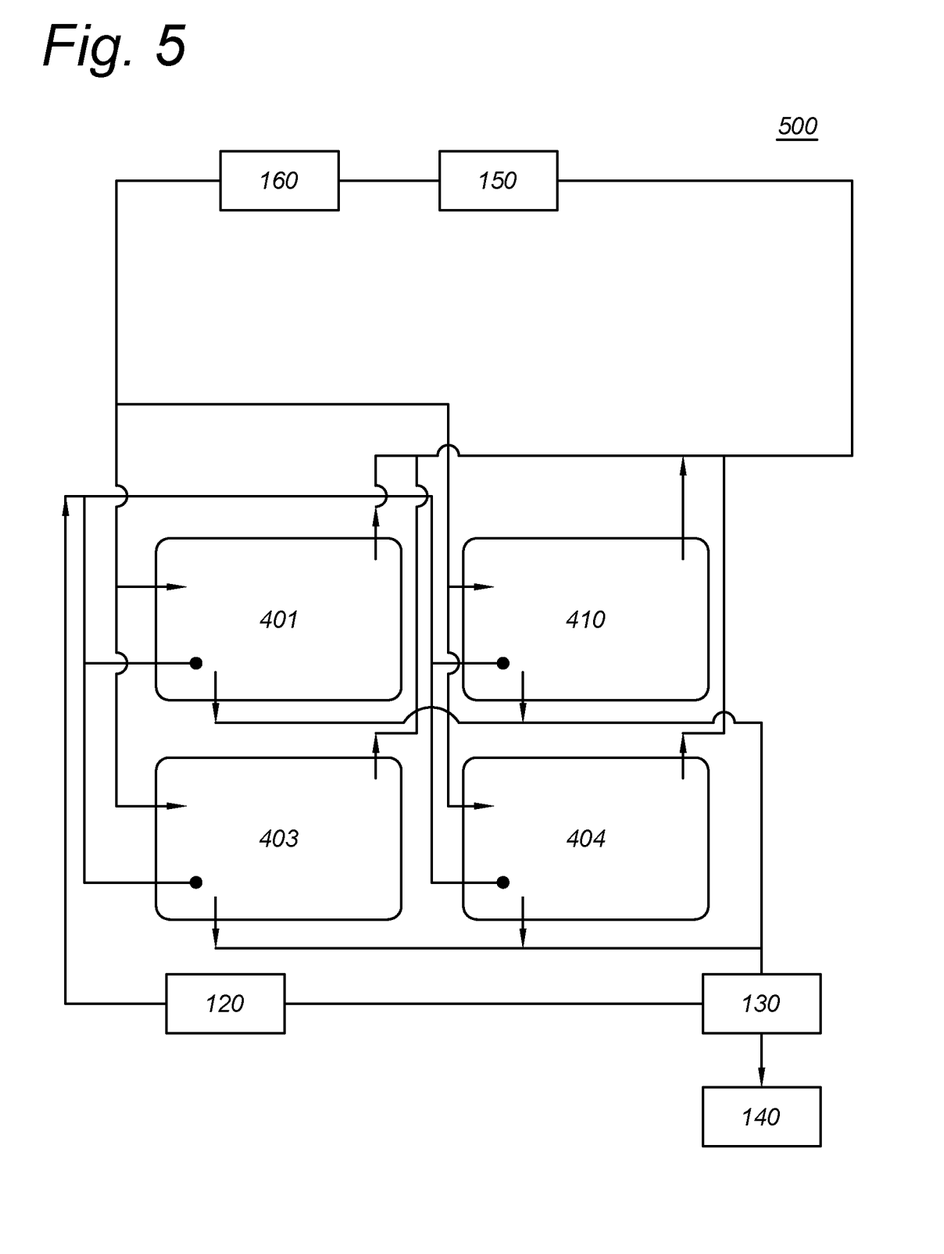
FIG. 5 illustrates an embodiment of an insect breeding device with a gas drying apparatus.

FIG. 5, shows the insect breeding device 500 of a third embodiment according to the invention. The insect cages in this embodiment are similar to those as described hereinbefore, for example insect cage 101, 301-304, 401, 403, 404, 410. The insect breeding device further comprises a gas drying apparatus drying the interior of each insect cage after the insect cages have been cleaned. Preferably, the interior of the insect cages is dried with air after cleaning of the insect cages. In an embodiment the insect breeding device 500 further comprises of a ventilator 150 and an air heater 160. The ventilator 150 generates a gas flow, where the gas is then heated at the heater 160. The heated gas is then transferred through a third pipe to supply air to the insect cages 401, 403, 404, 410 through a third opening of the insect cage. A fourth opening of the insect cage is used to return the gas to the ventilator 150.

In one embodiment, the insect cage further comprises of a third valve coupled to the third opening configured to open or close the third opening, and a fourth valve, coupled to the fourth opening, configured to open or close the fourth opening.

Figure 6:
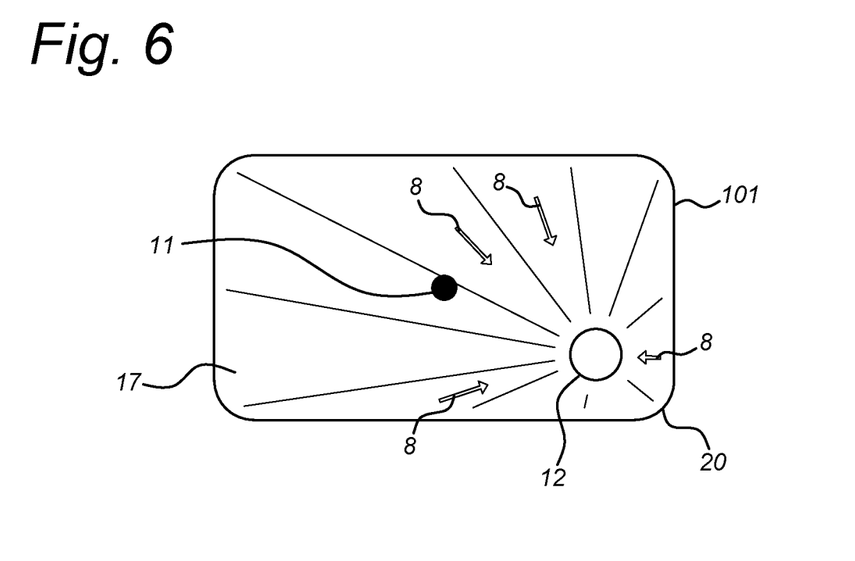
FIG. 6 illustrates an embodiment of a bottom side at the interior of an insect cage.

FIG. 6 shows an interior bottom floor 17 of the insect cage 101, which floor is a tapered floor 17. The insect cage has a closed top wall 16 (not shown). The floor comprises the opening 11, here located essentially in the center of the floor, and the second opening 12, here essentially located at or near a rounded corner 20 of the insect cage. Drainage of a fluid, such as the drainage 8 of the cleaning liquid comprising debris is directed from all sides and locations inside the insect cage, along the tapered floor surface towards the corner near which the second opening 12 is located. This interior bottom floor 17 can also be provided in the insect cages 301-304, 401,403,404,410 in the embodiments described herein before.

Figure 7:
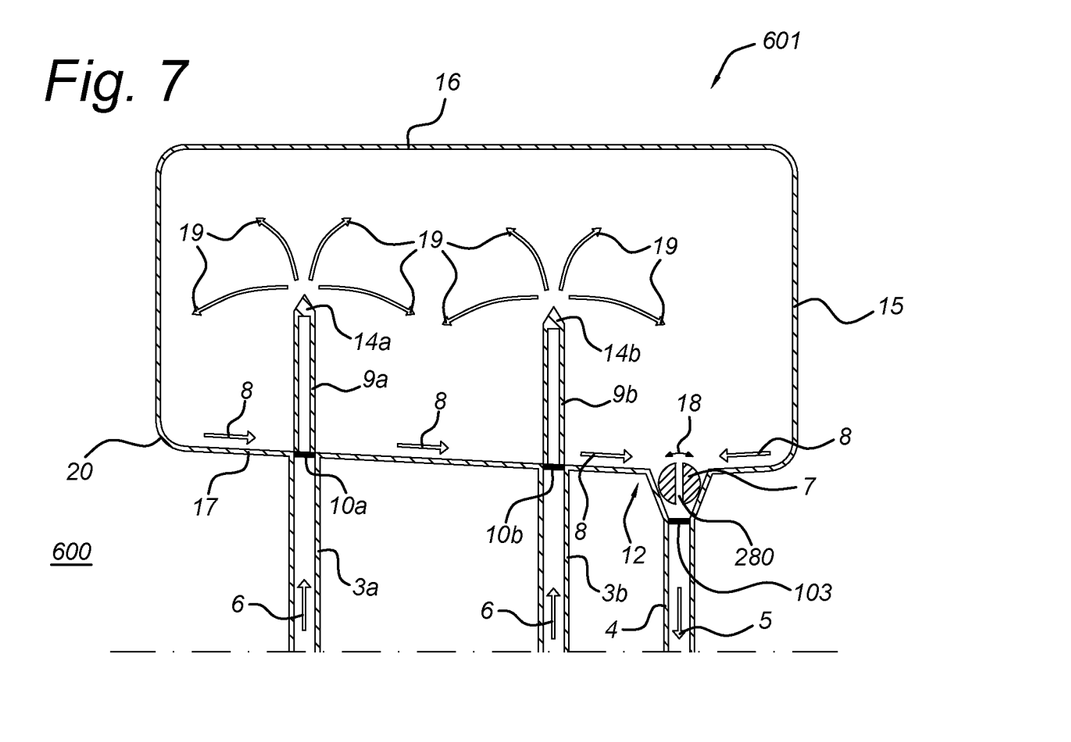
FIG. 7 illustrates an embodiment of an insect cage.

FIG. 7 shows the insect breeding device 600 of a fourth embodiment according to the invention, comprising insect cage 601. The insect breeding device encompasses at least an insect cage 601, said cage provided with two nozzles 14a and 14b, connected to pipes 3a and 3b through pipes 9a and 9b, respectively, the pipes 3a and 3b further provided with a valve 10a and 10b, respectively.

Figure 8A:
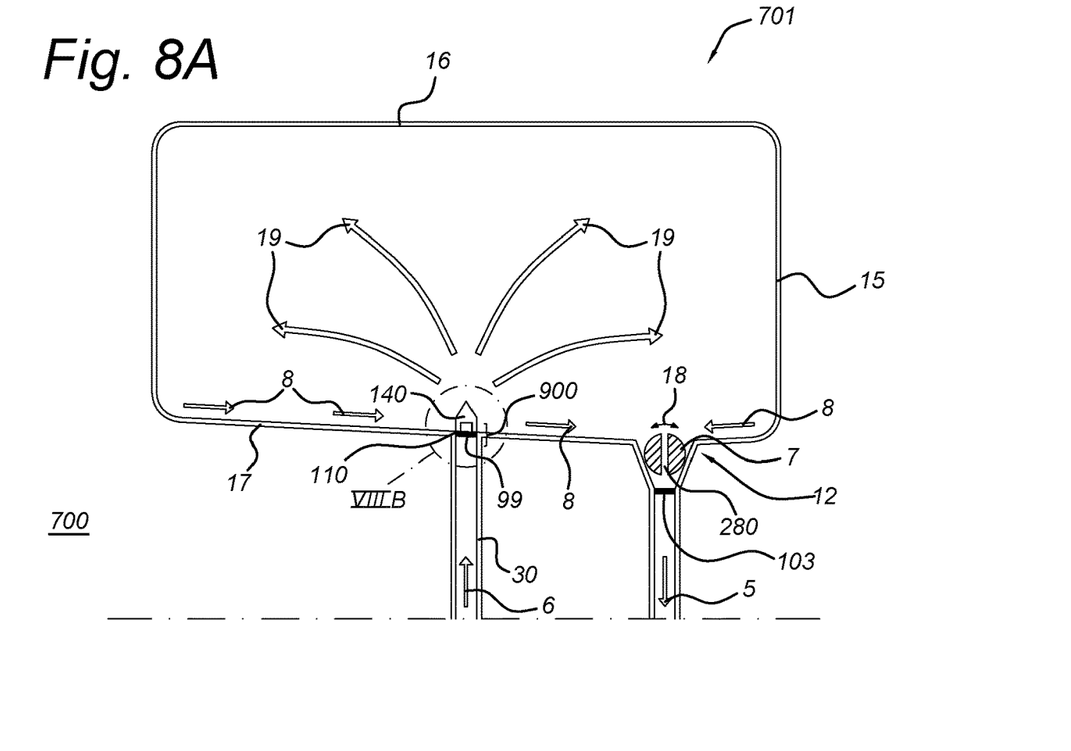
FIG. 8A illustrates an embodiment of an insect cage.
Figure 8B:
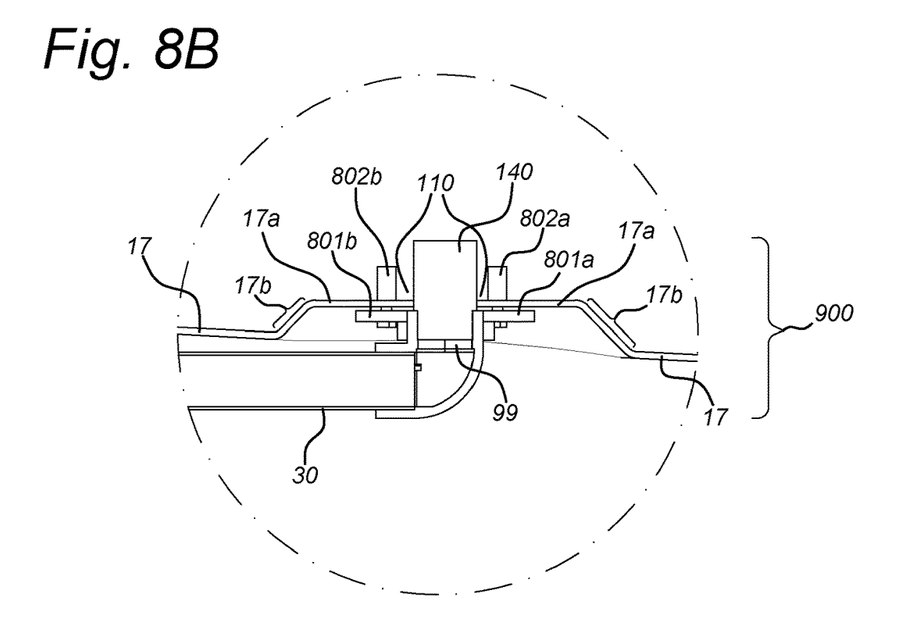
FIG. 8B illustrates an excerpt of the insect cage of FIG. 8A, zoomed in on a nozzle entering the interior of the insect cage.

FIG. 8A shows the insect breeding device 700 of a fifth embodiment according to the invention, comprising at least a cage 701. The insect breeding device comprises insect cage 701, said insect cage encompassing a nozzle 140 located at or near the surface of the bottom 17 at the inner side of the insect cage. The nozzle 140 is connected to pipe 30 through a connector 900 which embraces opening 110 in the bottom floor 17. The pipe 30 comprises valve 99 located in or near the opening 110. Cleaning liquid enters insect cage 701 in the direction 6 through pipe 30 and schematically flows 19 of cleaning liquid inside the insect cage are indicated. FIG. 8B shows an example of the connection between the nozzle 140 in the interior of the insect cage 701 and the pipe 30 connected to a reservoir of cleaning liquid (not shown). The connection is through connector 900. The floor 17 of the insect cage 701 has a protruded portion surrounding the opening 110. The protrusion in floor 17 comprises a portion 17b extending diagonally and upwardly in the direction of opening 110, relative to the main surface of the (tapered) floor 17 of the insect cage. The protrusion in floor 17 further comprises protruded portion 17a surrounding opening 110, and horizontally oriented. The portion 17b connects the main surface portion of floor 17 with the protruded portion 17a surrounding opening 110. Protruded portion 17a comprises one or more through-holes. The connector 900 comprises flanges 801a, 801b comprising a through-hole in communication with the through-hole(s) in protruded portion 17a of floor 17. The connector 900 connects pipe 30 and nozzle 140 by bolds 802a, 802b, provided through the through-holes in the protruded portion 17a of the floor and the through-holes in the flans 801a, 801b of the connector 900. This arrangement provides, a smooth floor 17, comprising nozzle 140, without presence of a ridge, a cavity, an edge, a ledge, etc., under which otherwise debris may accumulate, and/or under which otherwise insects such as ovipositioning black soldier flies may oviposite, i.e. lay eggs at undesired locations in the insect cage. That is to say, the connector 900 provided for a smooth inner surface of the insect cage, preventing accumulation of debris or eggs deposited at undesired locations. The nozzle 140 is for example alternatively positioned at the distal end of a pipe 9 connecting the nozzle and pipe 30, relative to the first opening 110 in the bottom wall of the cage 701. Then, the connector 900 connects pipe 30 and pipe 9.

While the invention has been described in terms of several embodiments, it is contemplated that alternatives, modifications, permutations and equivalents thereof will become apparent to one having ordinary skill in the art upon reading the specification and upon study of the drawings. The invention is not limited in any way to the illustrated embodiments. Changes can be made without departing from the scope which is defined by the appended claims.

The invention claimed is:

1. An insect breeding device comprising
    at least one insect cage;
    a bin for holding a cleaning liquid;
    a first pipe connected to the bin for receiving the cleaning liquid, wherein the pipe is entering the at least one insect cage through a first opening in the at least one insect cage;
    a nozzle, coupled to the first pipe, positioned inside the at least one insect cage configured to deliver the cleaning liquid to the interior of the at least one insect cage; and
    a second pipe, coupled to a second opening in the at least one insect cage, different from the first opening in the at least one insect cage, configured to drain the cleaning liquid and debris remaining from farming insects in the insect cage from the at least one insect cage, and
    a gas drying apparatus comprising:
        a ventilator for generating a gas flow;
        a heater for heating the generated gas flow;
        a third pipe coupled to a third opening of the insect cage for transporting the heated gas flow inside the at least one insect cage, and
        a fourth opening of the insect cage for transporting the gas out of the at least one insect cage.

2. The insect breeding device according to claim 1, comprising
    a liquid clearance device coupled to the second pipe and the bin, provided with
        a filter configured to separate the cleaning liquid from the debris and to deliver the cleaning liquid to the bin through a fifth pipe.

3. The insect breeding device according to claim 2, wherein the filter comprises
    a sieve configured to separate the debris from the cleaning liquid, and
    a debris receptacle, configured to collect the debris separated by the sieve.

4. The insect breeding device according to claim 1, wherein the cleaning liquid further comprises water and at least one non-foaming detergent.

5. The insect breeding device according to claim 4, wherein the cleaning liquid comprises between 0.5 percent and 10 percent of the non-foaming detergent by volume of the total cleaning liquid.

6. The insect breeding device according to claim 1, wherein
    the nozzle is a fluid nozzle consisting of one of: a spiral liquid spray nozzle, a full-cone nozzle, a deflector plate nozzle, a solid jet nozzle, and a nozzle with a rotating head.

7. The insect breeding device according to claim 1, further comprising
    a first valve, coupled to the first opening, configured to open or close the first opening, and
    a second valve, coupled to the second opening, configured to open or close the second opening.

8. The insect breeding device according claim 1, further comprising
    a first pump, positioned between the first opening and the bin, configured to deliver cleaning liquid to the interior of the at least one insect cage with at least one of a predetermined flow rate and a predetermined liquid pressure, and wherein the liquid pressure is preferably in the range of between 1.5 and 6 bar.

9. The insect breeding device according to claim 8, further comprising
    a second pump, positioned between the second opening and the bin, configured to drain the cleaning liquid and debris from the at least one insect cage to the bin.

10. The insect breeding device according to claim 9, further comprising
    a third valve coupled to the third opening configured to open or close the third opening, and
    a fourth valve coupled to the fourth opening configured to open or close the fourth opening.

11. The insect breeding device according to claim 10, further comprising a controller connected to the first valve and the second valve and the first pump and second pump, wherein the controller is arranged to switch between a first state and a second state; wherein in the first state the first and second valves are closed and the first and second pumps are switched off, in the second state, the first valve is open and the second valve is open, the first pump is switched on and the second pump is switched on.

12. The insect breeding device according to claim 11, further comprising a heater arranged between the bin and the first pump connected to the controller, wherein the heater is further arranged to deliver the cleaning liquid to the first pump at a temperature in the range of 31.5° C. and 32° C.

13. The insect breeding device according to claim 1, wherein the at least one insect cage has a substantially block shape having rounded corners in the inner surface of the cage and/or is manufactured using rotation molding of a polymer blend, preferably comprising polyethylene.

14. The insect breeding device according to claim 1, wherein the at least one insect cage further comprises a tapered surface on the surface coupled to the second opening.

15. The insect breeding device according to claim 1, wherein the cleaning liquid comprises a mixture of potassium, amine compounds, silicates, phosphates, non-ionogenic and amphoteric humidifiers and complexing agents.

16. The insect breeding device according to claim 1, wherein the nozzle is further configured to have a spray angle between 240 degrees and 300 degrees for a solid nozzle, or between 90 degrees and 120 degrees for a spiral nozzle, and a spray pattern arranged as a solid cone or solid jets from a sphere.

17. The insect breeding device according to claim 1, wherein the nozzle is arranged to be positioned centrally in the inner volume of the at least one insect cage.

18. The insect breeding device according to claim 1, wherein the at least one insect cage comprises a further nozzle, the nozzles being positioned off-center, in the inner volume of the cage.

19. The insect breeding device according to claim 1, comprising two insect cages stacked horizontally or vertically with each other.

20. An insect breeding device comprising at least one insect cage;

a bin for holding a cleaning liquid;

a first pipe connected to the bin for receiving the cleaning liquid, wherein the pipe is entering the at least one insect cage through a first opening in the at least one insect cage;

a nozzle, coupled to the first pipe, positioned inside the at least one insect cage configured to deliver the cleaning liquid to the interior of the at least one insect cage;

a second pipe, coupled to a second opening in the at least one insect cage, different from the first opening in the at least one insect cage, configured to drain the cleaning liquid and debris remaining from farming insects in the insect cage from the at least one insect cage, and a first pump, positioned between the first opening and the bin, configured to deliver cleaning liquid to the interior of the at least one insect cage with at least one of a predetermined flow rate and a predetermined liquid pressure.

21. An insect breeding device comprising at least one insect cage;

a bin for holding a cleaning liquid;

a first pipe connected to the bin for receiving the cleaning liquid, wherein the pipe is entering the at least one insect cage through a first opening in the at least one insect cage;

a nozzle, coupled to the first pipe, positioned inside the at least one insect cage configured to deliver the cleaning liquid to the interior of the at least one insect cage; and a second pipe, coupled to a second opening in the at least one insect cage, different from the first opening in the at least one insect cage, configured to drain the cleaning liquid and debris remaining from farming insects in the insect cage from the at least one insect cage, wherein the at least one insect cage further comprises a tapered surface on the surface coupled to the second opening.

* * * * *